United States Patent
Hochgraeber et al.

(10) Patent No.: US 9,329,157 B2
(45) Date of Patent: May 3, 2016

(54) SWITCHING VALVE FOR LIQUID CHROMATOGRAPHY

(71) Applicants: Hermann Hochgraeber, Offenberg-Neuhausen (DE); Burkhard Seyferth, Puchheim (DE)

(72) Inventors: Hermann Hochgraeber, Offenberg-Neuhausen (DE); Burkhard Seyferth, Puchheim (DE)

(73) Assignee: DIONEX SOFTRON GMBH, Germering, DE (US)

( * ) Notice: Subject to any disclaimer, the term of this patent is extended or adjusted under 35 U.S.C. 154(b) by 179 days.

(21) Appl. No.: 13/961,555

(22) Filed: Aug. 7, 2013

(65) Prior Publication Data

US 2014/0043018 A1 Feb. 13, 2014

(30) Foreign Application Priority Data

Aug. 10, 2012 (DE) .......................... 10 2012 107 377
Aug. 10, 2012 (DE) .......................... 10 2012 107 378
Aug. 10, 2012 (DE) .......................... 10 2012 107 379

(51) Int. Cl.
*F16K 25/00* (2006.01)
*G01N 30/26* (2006.01)
(Continued)

(52) U.S. Cl.
CPC ............ *G01N 30/26* (2013.01); *F16K 11/0743* (2013.01); *F16K 31/041* (2013.01); *F16K 31/043* (2013.01); *F16K 37/0025* (2013.01); *G01N 2030/202* (2013.01)

(58) Field of Classification Search
CPC ..... F16K 3/10; F16K 31/041; F16K 11/0743; G01N 30/26; G01N 30/22; G01N 2030/202
USPC ......... 251/205, 191, 192, 157, 304, 208, 209, 251/176; 137/625.17, 625.46, 625.47
See application file for complete search history.

(56) References Cited

U.S. PATENT DOCUMENTS

| | | | |
|---|---|---|---|
| 3,297,053 A | 1/1967 | McKinney | |
| 3,384,118 A | 5/1968 | Heintz et al. | |

(Continued)

FOREIGN PATENT DOCUMENTS

| | | |
|---|---|---|
| CN | 101457845 A | 6/2009 |
| CN | 102537473 A | 7/2012 |

(Continued)

OTHER PUBLICATIONS

Office Action mailed Aug. 4, 2014, in corresponding Japanese patent application No. 2013-148557.

(Continued)

*Primary Examiner* — John K Fristoe, Jr.
*Assistant Examiner* — Umashankar Venkatesan
(74) *Attorney, Agent, or Firm* — Timothy J. Ohara

(57) ABSTRACT

The invention relates to a switching valve for liquid chromatography having a stator in which multiple ports are formed. Each port is formed by in each case one duct which is connected at one end to in each case one connection port and which, at the other end, has a predetermined port opening cross section at a stator face surface of the stator. The switching valve includes a rotor which has a rotor face surface which interacts with the stator face surface and in which are formed at least one or more grooves. Depending on the rotational position of the rotor with respect to the stator, in at least one predetermined switching position, the switching valve connects respective predetermined port opening cross sections in a pressure-tight manner. The switching valve further includes a drive device for driving the rotor in rotation, and a device for detecting the rotational position of the rotor, which device generates a signal corresponding to the absolute or relative position of the rotor.

15 Claims, 3 Drawing Sheets

(51) Int. Cl.
*F16K 31/04* (2006.01)
*F16K 37/00* (2006.01)
*F16K 11/074* (2006.01)
*G01N 30/20* (2006.01)

(56) References Cited

U.S. PATENT DOCUMENTS

| | | | |
|---|---|---|---|
| 3,405,539 | A | 10/1968 | Tanaka |
| 3,542,071 | A | 11/1970 | Lightner et al. |
| 4,156,437 | A * | 5/1979 | Chivens et al. ............... 137/554 |
| 4,224,958 | A * | 9/1980 | Kaplan et al. ................ 137/340 |
| 4,444,066 | A | 4/1984 | Ogle et al. |
| 4,501,297 | A | 2/1985 | Baker |
| 4,741,508 | A * | 5/1988 | Fukamachi ..................... 251/71 |
| 4,754,949 | A * | 7/1988 | Fukamachi ............. 251/129.03 |
| 5,566,715 | A * | 10/1996 | Griffin .................... 137/624.11 |
| 5,927,682 | A * | 7/1999 | Gul et al. ......................... 251/77 |
| 6,491,063 | B1 | 12/2002 | Benatav |
| 7,195,229 | B2 * | 3/2007 | Maeda ......................... 251/205 |
| 2006/0260695 | A1 | 11/2006 | Keene et al. |
| 2007/0246109 | A1 * | 10/2007 | Wolf et al. ............... 137/625.21 |
| 2009/0159823 | A1 | 6/2009 | Matsunaga et al. |
| 2010/0276617 | A1 | 11/2010 | Yasunaga |
| 2010/0281959 | A1 | 11/2010 | Berndt |
| 2012/0061604 | A1 | 3/2012 | Nowak |
| 2014/0182686 | A1 * | 7/2014 | Bassi et al. ......................... 137/1 |

FOREIGN PATENT DOCUMENTS

| | | |
|---|---|---|
| DE | 438244 | 12/1926 |
| DE | 2934346 A1 | 11/1980 |
| DE | 102011000104 B4 | 2/2013 |
| EP | 0356420 A2 | 8/1989 |
| EP | 1304516 A2 | 4/2003 |
| EP | 2381124 A1 | 10/2011 |
| GB | 2043207 A | 4/1983 |
| GB | 2164124 A | 3/1988 |
| JP | 54127036 | 10/1979 |
| JP | 586263 | 1/1983 |
| JP | S58-067175 | 5/1983 |
| JP | H1-81568 | 5/1989 |
| JP | H5-83550 | 11/1993 |
| JP | H6-324025 | 11/1994 |
| JP | 2007516394 | 6/2007 |
| WO | 9616277 A1 | 5/1996 |
| WO | 2005047826 A2 | 5/2005 |
| WO | 2009101695 A1 | 8/2009 |
| WO | 2011008657 A2 | 1/2011 |
| WO | 2011014310 A1 | 2/2011 |
| WO | 2012095097 A1 | 7/2012 |

OTHER PUBLICATIONS

U.S. Appl. No. 13/979,407.

* cited by examiner

SWITCHING VALVE FOR LIQUID CHROMATOGRAPHY

CROSS-REFERENCE TO RELATED APPLICATION

This application claims the priority benefit under 35 U.S.C. §119 to German Patent Application No. 10 2012 107 377.5, filed on Aug. 10, 2012; German Patent Application No. 10 2012 107 378.3, filed on Aug. 10, 2012; and German Patent Application No. 10 2012 107 379.1, filed on Aug. 10, 2012, which are incorporated herein by reference.

FIELD OF THE INVENTION

The invention relates to a switching valve for liquid chromatography, in particular a high-pressure switching valve for high-performance liquid chromatography (HPLC).

BACKGROUND

In HPLC, a sample to be examined must be fed into a high-pressure liquid stream which is then supplied to the chromatography column. The chromatography column is normally kept at a constant temperature, which may amount to up to 110° C. and in the near future even up to in the region of 150° C., in a column oven. As a result of the temperature control of the column, a higher value for the flow through the column is attained at a given pressure. This yields shorter processing times.

To attain short capillary paths between a sample input device, the switching valve for the introduction of the sample volume into the fluid stream and the column, it is desirable for the switching valve to be positioned as close as possible to the column, preferably on or in the column oven. The switching valve must accordingly exhibit relatively high temperature resistance.

Whereas the purely mechanical components of a switching valve, in particular of a high-pressure switching valve for HPLC, have no problems or few problems with regard to temperature resistance, problems are encountered in attaining the desired temperature resistance of electronics components, in particular for the detection of the rotational position of a mechanical part of the switching valve.

Switching valves for introducing a sample into the fluid stream normally have a stator in which there are provided multiple connection ports for the supply and discharge of the fluid to and from the switching valve. The ports are connected via ducts to opening cross sections which are formed on a switching surface of the stator, for example in the face side of a substantially cylindrical stator element. The rotor likewise has a switching surface which interacts with the switching surface of the stator, wherein in the switching surface of the rotor there are formed grooves which serve to connect certain opening cross sections and/or ports of the stator to one another as a function of two or more switching positions. Here, the rotor and the stator must be pressed against one another with an adequately high pressing force in order to attain a sealing action in the plane of the switching surfaces even in the case of high pressures such as arise in liquid chromatography, in particular HPLC.

Such switching valves are described for example in WO 2009/101695 or US 2010/0281959 A1.

In the case of valves constructed in this way, it is necessary for the position of the rotor, which is normally driven in rotation by a suitable drive unit, for example an electric motor with a gearing, to be detected with sufficient accuracy in order that the switching positions formed by the rotor and the stator can be moved to with sufficient accuracy.

For this purpose, known switching valves have electronics for detecting the position of the rotor. Said electronics are normally arranged spatially in the vicinity of the rotor. Here, the position of the rotor may in particular be detected optically. Here, optical marks are provided on the rotor itself, which optical marks can be detected by means of a photodetector, for example a photodiode.

The use of such photoelectric or electric (for example capacitive) sensors however poses problems at temperatures considerably higher than 70° C. For this reason, such switching valves cannot be positioned entirely in the column oven, at least not with the switching valve head in which the rotor and the stator are provided. This is however desirable because switching valves are commonly arranged in a wall of the column oven, wherein the column oven for this purpose has corresponding apertures in the wall, into which apertures in each case one switching valve can be inserted. Here, the switching valve head is situated on the inner wall of the column oven or projects into the interior of the column oven so as to permit the connection of capillaries to the respective ports of the switching valve.

To solve said problem, it is known for the movement of the rotor to be limited by means of stops, such that the switching position which is delimited by the stops can be moved to in an exact manner. This is however possible only in the case of switching valves which have two switching positions. Furthermore, it is possible for the mechanical stops to be used for the calibration of the position detection device, in order hereby to allow for temperature-induced deviations. In the case of such valves, it is thus not necessary for position detection by means of a corresponding sensor device to be provided directly at the rotor.

However, in the case of such switching valves, it is necessary to carry out calibration processes which entail a corresponding amount of effort, in particular are time-consuming.

SUMMARY

The invention is therefore based on the object of providing a switching valve for liquid chromatography, in particular a high-pressure switching valve for high-performance liquid chromatography, which switching valve exhibits improved temperature resistance while simultaneously being of a compact structural size.

The invention is based on the realization that the rotational movement of the rotor or the absolute position of the rotor can be transmitted by means of a transmission element into an axially rear region of the switching valve, in which the absolute or relative position or the rotational movement of the transmission element is then detected by means of a device for detecting the rotational position of the rotor. Depending on the detected position, the device for detecting the rotational position of the rotor generates a signal which can be used in particular for the automated control of the switching positions of the switching valves.

As a result of the relocation of the detection position for the rotational position of the rotor into the rear region of the switching valve, the electronics required for the detection can be provided in a region which is at a sufficient distance from the head region of the switching valve, which is commonly exposed to temperatures of up to 150° C.

Said rear region may in particular be at such an axial distance from the head region of the switching valve in which the rotor is arranged that said region is arranged outside the interior of the column oven even when the switching valve is mounted in a wall of the column oven. Even the case of a temperature of 150° C. at the head region of the valve, the temperature in the rear region in which the sensor device is provided may lie considerably below that, in particular in a temperature range below 70° C., in which temperature resistance of an electronic circuit can still be readily attained.

The transmission element can preferably be moved in a substantially load-free manner, such that the transmission element is not acted on by any relevant torsional forces that would lead to an inaccuracy in the detection of the rotational position.

The transmission element is rotationally conjointly connected by way of its front end preferably coaxially to the rotor or to a coupling element which is coupled substantially rotationally conjointly to said rotor. In this way, the rotational movement of the rotor can be transmitted in a simple manner and in an extremely small space into a rear region.

According to the invention, the device for detecting the rotational position of the rotor (23) is designed and arranged so as to detect the rotational position of the transmission element (51) in a region facing away from the rotor (23), preferably in a rear end region of the transmission element (51).

In one embodiment of the invention, the transmission element may be in the form of a bar-shaped element. Said bar-shaped element may in particular have a diameter of only a few millimeters and extend, by way of its rear end, into a rear region of the switching valve facing axially away from the rotor.

Said rear region of the switching valve may exhibit predetermined thermal decoupling with respect to the axially front region of the switching valve in which the rotor and the stator are situated. In particular, the housing of the switching valve may for this purpose have ventilation slots in a region situated in front of the rear region of the switching valve, such that a cooling action is provided by a corresponding airflow through the housing and through the components situated therein.

It is self-evidently also possible in a central region of said type for thermal insulation to be provided by means of an insulation material which is arranged in the housing.

The insulation material may extend over the entire cross section of the housing and be in the form, for example, of an insulation plate which has an opening only for the passage of the transmission element.

In one embodiment of the invention, the transmission element may be composed of a thermally insulating material or a material which exhibits poor heat conduction, for example plastic or ceramic.

If the transmission element is in the form of a bar-shaped element and has only a diameter of a few millimeters, for example a diameter of less than 3 mm, preferably less than 2 mm, then it is also possible, for example, for high-grade steel to be used as a metal which exhibits relatively poor heat conduction.

In a further embodiment of the invention, the drive device for the switching valve may be provided axially adjacent to the region in which the rotor or the coupling element connected to the rotor is arranged. According to invention, the transmission element is in this case designed so as to also extend axially through the drive device, in particular coaxially with respect to the axis of the rotor.

In this case, the drive axle of the drive device may be of hollow design, wherein the bar-shaped transmission element extends through the hollow drive axle.

The drive device may have a planetary gear set which is provided between the drive itself and the valve head in which the rotor is arranged. The drive itself may for example be in the form of an electric motor, pneumatic actuator or hydraulic actuator. In such a situation, the transmission element is preferably in the form of a bar-shaped element and extends through one or more sun gears of the planetary gear set, which for this purpose have a hollow axle.

This yields an extremely compact and simple design.

In one embodiment of the invention, the device for detecting the rotational position of the rotor may be arranged radially in the region of the rear end of the transmission element. The transmission element or a marker element connected thereto may for this purpose have markings on a circumferential surface, which markings are sensed by a likewise radially arranged sensor element.

In another embodiment of the invention, the device for detecting the rotational position of the rotor may be provided at the face side on the rear end of the transmission element.

For this purpose, the device for detecting the rotational position may have a marker element arranged rotationally conjointly on the rear end of the transmission element, which marker element has an axially oriented surface which preferably projects beyond the face-side end of the transmission element. On said surface there may be provided markings which are detected by means of a sensor element, such that the device for detecting the rotational position of the rotor is capable of determining the relative or absolute rotational position of the marker element from the signal of the sensor element.

For this purpose, the marker element may be in the form of a radially magnetized marker element. The sensor element may be in the form of a Hall sensor element, the sensor surface of which is situated opposite the face surface of the magnet element and detects the position thereof contactlessly.

The use of a magnetic marker element, for example a radially or diametrically magnetized magnet element and of a Hall sensor offers the advantage that said components are likewise available with extremely high temperature stability. The electrical signal provided by said components can thus be transmitted via lines to a superordinate evaluation and control unit, which may be at an even greater distance from the head of the switching valve.

BRIEF DESCRIPTION OF THE DRAWINGS

The invention will be explained in more detail below on the basis of exemplary embodiments illustrated in the drawing, in which.

DETAILED DESCRIPTION OF EMBODIMENTS

Figure 1:
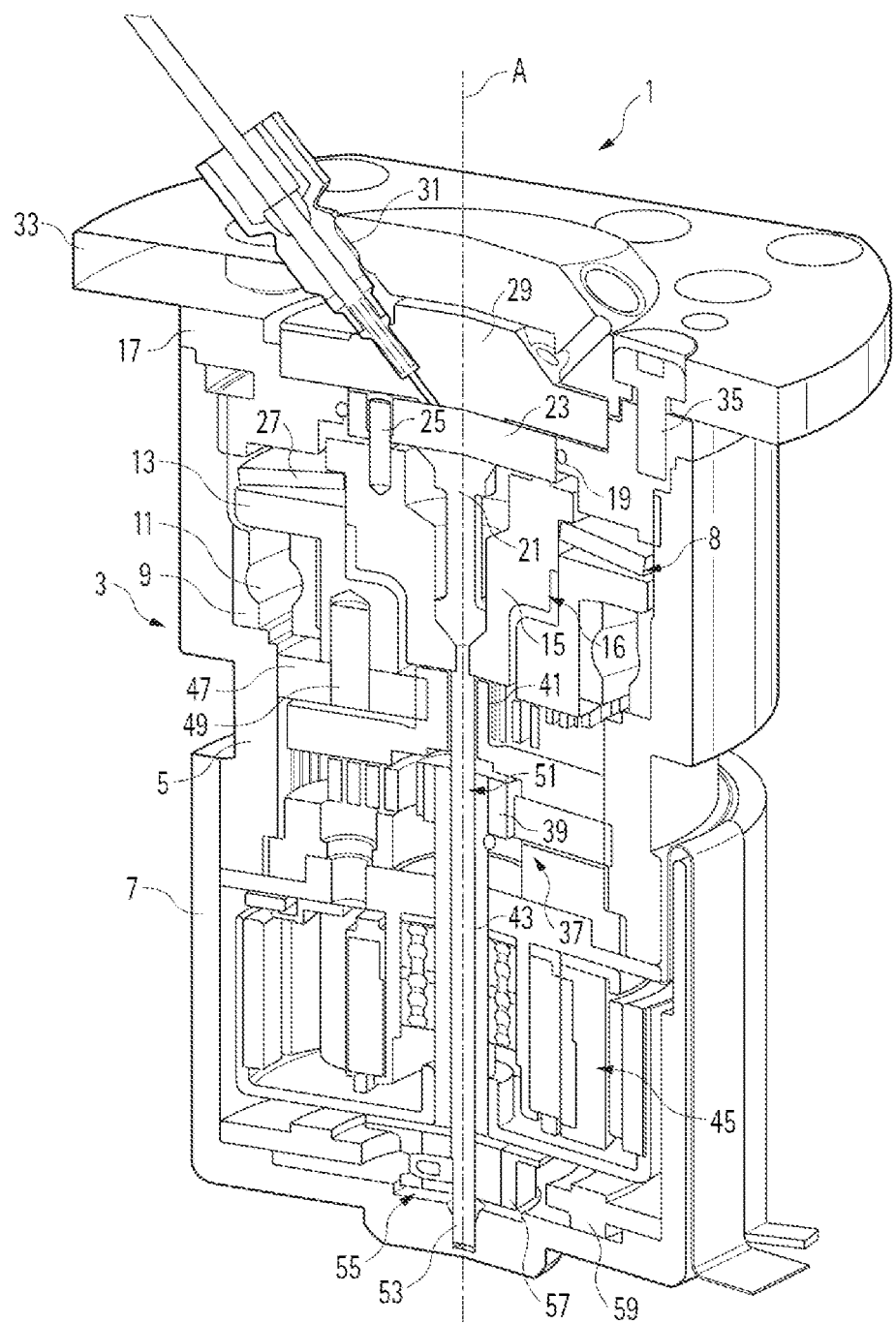
FIG. 1 is a perspective, cut-away illustration of a first embodiment of a switching valve according to the invention.

The switching valve 1 illustrated in FIG. 1 is composed of a housing 3 which has a first housing part 5 and a second housing part 7. In the second, pot-shaped, housing part 7 there is accommodated a drive unit 45, for example in the form of an electric motor. In the first housing part 5, the switching valve itself is accommodated in the upper region and a gearing unit 37 is accommodated in the lower region, which gearing unit is coupled to the drive unit 45. The first housing part 5 is closed off by means of a first cover part 17 and a second cover part 33.

The switching valve itself is composed of a stator 29, a rotor 23, and a bearing and pressing device 8 for the rotatable mounting of the rotor 23 in the housing 3 and the generation of a pressing force with which the rotor is acted on in the direction of the stator. In a known way, the stator has port opening cross sections, formed in the stator face surface, of connection ports 31 for the supply and discharge of the medium to be controlled. The stator face surface interacts with a rotor face surface of the rotor 23, in which grooves are formed. Depending on the angular position of the rotor 23 relative to the stator 29, the grooves provided in the stator end surface connect in each case predetermined port opening cross sections, such that in each case the relevant connection ports 31 are fluidically connected.

In the embodiment illustrated in FIG. 1, the bearing and pressing device 8 is composed of a bearing 11, a receiving part 13, a spring unit 27 and a coupling unit 16.

The first housing part 5 has, in its interior, a shoulder 9 on which the annular bearing 11 is supported axially. The bearing 11 is in the form of a radial bearing with adequate load-bearing capacity in the axial direction, for example an angular-contact ball bearing. The substantially hollow-cylindrical or pot-shaped receiving part 13 is supported, by way of a flange which extends radially into the housing interior almost as far as the inner wall of the housing 3 or of the housing part 5, on the bearing 11, such that the receiving part 13 is mounted so as to be fixed in the axial direction and rotationally movable. Here, the flange or the bearing 11 must self-evidently be designed such that the parts which are movable relative to one another do not come into contact, so as to permit an unhindered rotational movement. In the example illustrated, a small axial annular gap is thus provided between the outer ring of the bearing 11 and the flange of the receiving part 13.

The coupling unit 16, which is composed of a coupling element 15 and a compensation element 21, is of substantially hollow cylindrical or pot-shaped form, and extends by way of its lower region into the receiving part 13. The coupling element 15 has an outer contour which substantially corresponds to the contour of the interior of the receiving part 13. The coupling part 15 is thus guided displaceably in the axial direction by the receiving part 13.

In the embodiment of a switching valve 1 illustrated in FIG. 1, the inner diameter of the interior of the receiving part 13 is selected so as to substantially correspond to the outer diameter of the coupling element 15, such that adequately precise centering of the coupling element 15 in the radial direction relative to the receiving part 13 and thus relative to the valve axis A is attained. This is because both the stator 29, by way of its longitudinal axis (which runs perpendicular to the stator face surface and coaxially with respect to the port opening cross sections), and also the rotor 23, by way of its axis of rotation, must be aligned as precisely as possible with respect to one another such that the stator axis and the rotor axis are in alignment (and form the valve axis). At the same time, through mutually corresponding selection of the outer diameter of the coupling element 15 and of the inner diameter of the receiving part 13, precise axial displaceability of the coupling element 15 in the valve axis is attained. This however entails correspondingly low manufacturing tolerances.

In the embodiment of a switching valve 1 illustrated in FIG. 1, the coupling element 15 is rotationally conjointly connected to the receiving part 13 merely by frictional locking, and is mounted so as to be rotationally movable together therewith by means of the bearing 13. The pressing force required for the frictional locking corresponds to the pressing and/or sealing force which acts at the boundary between the rotor 23 and the stator 29 and which is generated by the spring unit 27. In the embodiment illustrated, the spring unit is realized as a single annular spring element. It is self-evidently possible for a stack of annular spring elements to be used instead of a single annular spring element.

To realize the frictional locking, the coupling element 15 has, in its upper region, a flange which extends radially outward over the circumference, which flange rests by way of its underside on the annular spring unit 27 in the form of the annular spring element 27. The spring element 27 is arranged in the annular region between the outer wall of the coupling element 15 and the inner wall of the first housing part 5, and is supported against the annular face surface of the receiving part 13 or the face surface of a radially outwardly running flange of the receiving part 13.

The rotationally conjoint connection between the coupling element 15 and the receiving part 13 may also be realized by virtue of positive locking being provided between the two parts, in particular through the formation of projections or grooves in the inner wall of the receiving part 13 and correspondingly complementary interacting grooves or projections on the outer circumference of the coupling element 15. The positive locking must however be realized such that an axial movement of the coupling element is permitted.

The rotationally conjoint connection between the coupling element 15 and the receiving part 13 may also be realized indirectly by means of positive locking between the receiving part 13 and the spring unit 27 and between the spring unit 27 and the coupling element 15.

The axial securing of the bearing and pressing device 8 in the substantially hollow cylindrical first housing part 5 is realized by means of a first cover part 17 screwed into the upper opening of the first housing part 5. The first cover part 17 is of substantially annular form and engages by way of a shoulder 19 over the upper face side of the coupling element 15, which is likewise of substantially hollow cylindrical or pot-shaped form, wherein the interior of the coupling element 15 has a tapering diameter in its lower region. The compensation element 21 in the form of a wobble bar is provided in the interior of the coupling element 15. The compensation element 21 has a substantially rigid, flexurally stiff head region, a foot region which, in the illustrated exemplary embodiment, is likewise of substantially rigid and flexurally stiff form, and a bending region provided between the foot region and head region. The compensation element 21 is supported by way of its lower end or the foot region in the interior of the coupling element 15 and projects by way of the upper end side of the head region slightly beyond the upper annular face side of the compensation element 21. As can be seen from FIG. 1, the compensation element 21 or the wobble bar is received coaxially in the coupling element 15, which in turn is received coaxially in the receiving part 13. The compensation element 21 may also be pressed by way of its foot region into the coupling part 15. In this way, precise machining of that face surface of the compensation element 21 which faces toward the stator 23 is possible in the pressed-in state. In particular, the projecting length of the face surface of the compensation element 21 in relation to the annular face surface of the coupling element 15 can be set in a precise manner by means of retroactive machining in the pressed-in state.

The rotor 23 is received in the central opening of the annular first cover part 17, wherein the outer diameter of the cylindrical rotor 23 substantially corresponds to the inner diameter of the annular cover part 17. The receiving opening however serves not for guiding the rotor 23 but rather for sealing off the interior of the housing 3 or of the housing part 5 with respect to dust, moisture and other environmental influences. For this purpose, a sealing ring may be provided in a groove formed in the inner wall of the recess, which sealing ring acts on the circumferential wall of the rotor 23 and thus provides the desired sealing action. Instead of the bores for the pins 25, the rotor 23 may also have corresponding blind holes. This yields the advantage that the bearing and pressing device 8 is sealed off with respect to the rotor face surface and, for example, no lubricant can escape to the outside from the interior of the bearing and pressing device 8.

The rotor has three axial bores which serve for receiving in each case one connecting bolt 25. The connecting bolts 25 engage by way of an upper region into the respective bore in the rotor 23 and by way of a lower end region into a corresponding bore in the face surface of the coupling element 15. In this way, the rotor is coupled rotationally conjointly to the coupling element 15. At the same time, the bores in the rotor are formed such that the rotor 23 and thus the rotor face surface are held such that they can perform a tumbling movement through a small but sufficient angular range.

The cover part 17 has, in its upper region, a receiving region for the stator 29, which is likewise of substantially cylindrical form and has multiple radially obliquely inwardly running ducts into which in each case the front end of a connection port 31 that can be screwed into a second cover part 33 extends. Of the connection ports 31, only a single connection port 31 is illustrated in FIG. 1 because the two other connection ports are situated in the respectively cut-away part of the illustration. In the same way, only a single one of the connecting bolts 25 is visible in FIG. 1. The second cover part 33 engages over the stator 29 and presses the latter by way of its stator face surface against the rotor face surface when the second cover part 33 is connected by means of screws 35 to the first cover part. The bearing and pressing device 8 and the first housing part 5 and the first and second cover parts 17, 33 are coordinated with one another here such that an adequate pressing force is generated. For the assembly of the switching valve 1, it is self-evidently also possible for the first and second cover parts 17, 33 to firstly be connected to one another, and for the cover part as a whole to then be screwed, together with the stator held therein, into the housing 3 or the first housing part 5.

For the mounting of the valve head, the bearing 11 is firstly introduced into the interior of the first housing part 5. Subsequently, the receiving part 13, the spring unit 27 and the coupling element 15 with the compensation element 21 pressed therein are inserted into the first housing part. Subsequently, the first cover part 17 is screwed on such that the above-mentioned components are fixed in the interior of the first housing part 5. Subsequently, the rotor 23 can be inserted. The cover part 17 is formed, with regard to the axial thickness of its inner region, such that the rotor 23, after the mounting onto the connecting bolt 25, still projects slightly by way of its upper face surface, in which the grooves (not illustrated in any more detail) are provided, beyond the face-side surface of the cover part 17, which supports the stator 29. Subsequently, the stator 29 is placed onto the rotor 23 such that the lower face side of the stator, in which the opening cross sections of the ducts connected to the connection ports 31 are provided, rests on the upper face surface of the stator 23. It must be taken into consideration here that the central region of the stator face surface in which the opening cross sections of the ports are situated, and which must be sealed off with respect to the rotor face surface (which is normally, on the whole, planar), is normally formed so as to be raised slightly in relation to the surrounding region of the stator face surface. The sealing surface between the rotor and stator is thus defined by the size of the raised region of the stator face surface.

The second cover part 33 is subsequently placed on, which second cover part is designed so as to act on the upper side of the stator 29. The second cover part 33 is connected to the first cover part 17 by means of the screws 35, whereby the stator 29 is acted on with an axial force such that an axially acting sealing force is generated which is sufficient to seal off the grooves provided in the rotor 23 with respect to the stator face surface or the central, raised region of the stator face surface even at the high pressures prevailing in the HPLC. The pressure force is generated here by the spring unit 27 in the form of the annular spring element and/or by the screwing-on of the second cover part 33.

As already described above, the compensation element 21 in the illustrated embodiment has an adequately rigid head region and an adequately rigid foot region which are not deformed, or are at most scarcely (elastically) deformed, under the pressing force to be transmitted from the coupling element 15 to the rotor 23. By contrast, the interposed cylindrical bending region permits an elastic bending deformation such that the upper face surface, by which the compensation element 21 acts on that surface of the rotor 23 which faces towards it, can jointly perform possible wobbling movements of the rotor, and here, the contact pressure at the contact surface between the upper face surface of the compensation element 21 and the rotor 23 is substantially uniformly distributed. Furthermore, the compensation element 21 acts on the rotor 23 coaxially, such that, in the likewise coaxial pressing surface between the rotor 23 and the stator 29, a substantially uniform pressure distribution is attained even if the rotor 23 performs a wobbling movement about its axis during a rotation because the stator face surface and/or the rotor face surface do not run exactly perpendicular to the axis of rotation of the rotor 23.

Here, the bending region of the compensation element 21 must self-evidently also be sufficiently pressure-resistant that the desired pressing force can be transmitted to the rotor 23. Said region must thus be designed to be at least as rigid as the spring unit 27 in the axial direction. It is only adequate bending elasticity that is desired.

It is pointed out at this juncture that the foot region of the compensation element 21 need not imperatively be of flexurally stiff form. Said foot region may be in the form of an elongation of the bending region, such that the bending region and foot region are combined to form one region with identical or very similar characteristics. A rigid foot region however facilitates the coaxial support with respect to the element which transmits the pressing force, in this case the coupling element 15. Furthermore, a rigid, flexurally stiff foot region can facilitate the pressing of the compensation element 21 into the coupling element 15.

In another embodiment which is not illustrated, it is also possible to dispense with a specially designed head region, wherein the bending region and head region may have the same cross section.

Figure 2:
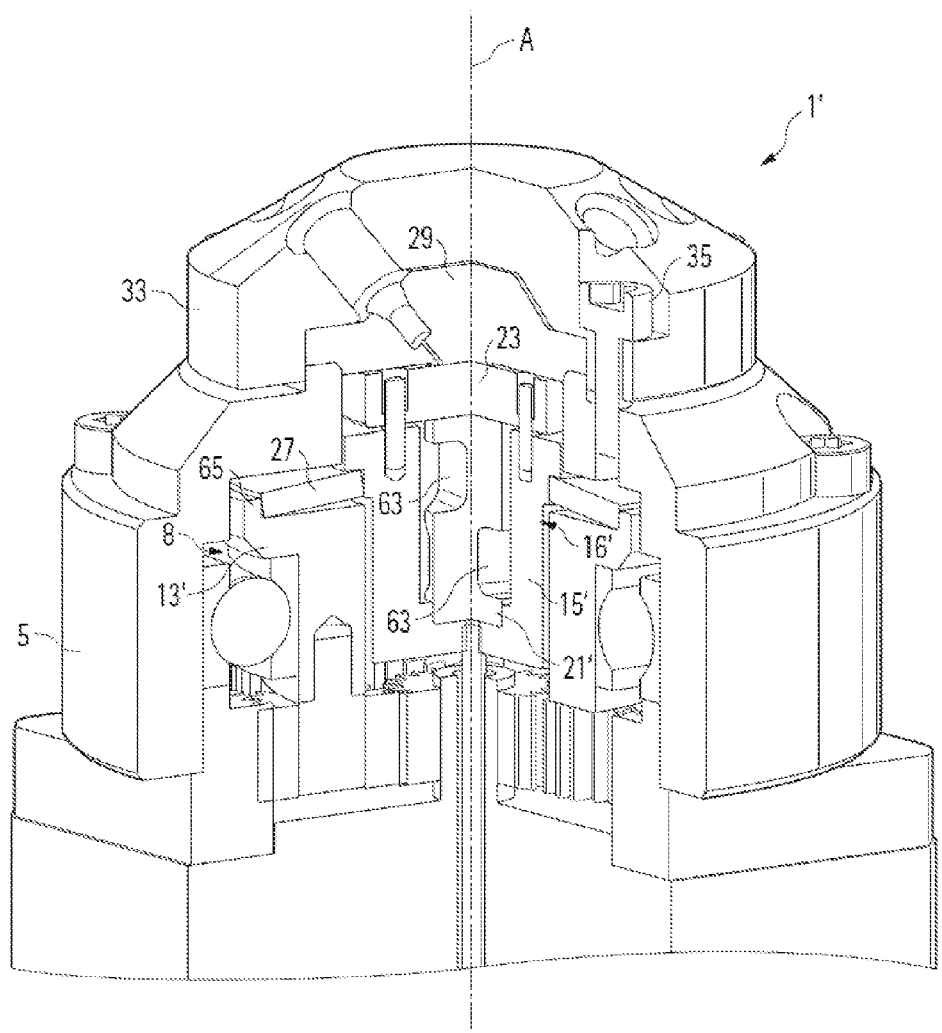
FIG. 2 is a perspective, cut-away illustration of the switching valve itself (without drive device) of a second embodiment of a switching valve according to the invention.

In the embodiment illustrated in FIG. 2 of a valve 1' according to the invention, substantially only the upper part is illustrated, that is to say the valve itself which is accommodated in the first housing part 5.

Said embodiment substantially equates to the embodiment in FIG. 1 and differs substantially only in two crucial aspects.

Firstly, the compensation element 21' is designed differently. Secondly, the centering of the coupling element 16' is realized no longer by means of an axially displaceable and radially fixed mounting of the coupling element 15' in the receiving part 13.

Instead of a cylindrical bending region with a relatively small diameter, the compensation element 21' has two bending regions, offset with respect to one another by 90° about the longitudinal axis, in the form of constrictions 63. In the embodiment illustrated in FIG. 2, the constrictions have a constant thickness and run parallel and symmetrically with respect to the longitudinal axis of the compensation element 21'. The constrictions 63 may however also be of any other form suitable for ensuring respectively adequate bending elasticity in the direction perpendicular to the surface of the constriction or to the longitudinal plane of extent thereof (in the case of a symmetrical embodiment of the plane of symmetry). It is also possible for the axial length of the constrictions 63 to be reduced to such an extent that they are practically in the form of solid joints with corresponding pivot axes running perpendicular to one another.

The compensation element 21' designed in this way thus also permits a wobbling movement of the rotor 23 and simultaneously transmits the required axial pressing force to the rotor 23.

For the centering of the coupling unit 16', the outer diameter of the coupling element 15' is selected to be slightly smaller than the inner diameter of the interior of the receiving part 13, such that at least pre-centering of the coupling element 15' and thus also of the coupling element 16' and of the rotor 23 in the radial direction relative to the receiving part 13 is generated.

The annular spring element 27, which again is in the form of a plate spring, is supported by way of its outer circumference in the radial direction against an encircling axial edge 65 of the radially extending flange of the receiving part 13'. By way of its inner surface of the annular chamber, the spring unit 27 acts on the outer circumference of the coupling element 15', wherein the diameter of the respective region of the coupling element 15' even in the unloaded state substantially corresponds to the inner diameter of the spring unit 27. During the assembly of the switching valve 1', the spring unit 27 is compressed axially such that the inner diameter is reduced and the spring unit 27 acts on the coupling element 15' with a radially inwardly directed force and in this way effects the centering of the coupling unit 16'.

The mode of operation of the switching valve 1' otherwise corresponds to the mode of operation of the switching valve 1 illustrated in FIG. 1, such that in this regard, reference is made to the statements made above.

The following description applies to both variants of switching valves 1, 1' as per FIGS. 1 and 2, wherein the description is given only with reference to FIG. 1, and can be transferred analogously to the embodiment as per FIG. 2.

In the embodiment illustrated in FIG. 1, in the lower region of the first housing part 5, there is provided a planetary gear set which, in the exemplary embodiment illustrated, has two transmission ratio stages. The gearing unit in the form of the planetary gear set therefore has two sun gears 39, 41 which have in each case a hollow axle. A hollow cylindrical drive output shaft 43 of a drive unit 45 is inserted into the hollow axle of the sun gear 39. The sun gear 39 is connected rotationally conjointly to the drive output shaft 43. The drive unit 45 and the gearing unit 37 together form the drive device for the rotational movement of the rotor 23 of the switching valve 1.

Of three planet gears or planet wheels 47 of the second stage of the planetary gear set, only one planet wheel 47 is visible in FIG. 1. Each planet wheel 47 has a coaxial pen 49 which engages into a corresponding receiving bore in the lower face side of the wall of the receiving part 13. In this way, each of the planet wheels 47 and thus the entire drive output of the planetary gear set, is connected to the receiving part 13, such that the receiving part 13 can hereby be driven in rotation.

A transmission element 51 in the form of a bar-shaped element 53 is guided through the hollow cylindrical drive output shaft 43 of the drive unit 45 and through the sun gear 41. The bar-shaped element engages by way of its upper end into the lower receiving opening of the coupling element 15 and is connected rotationally conjointly to the coupling element 15, for example by adhesive bonding, welding or the like.

As can be seen from FIG. 1, the bar-shaped element 53 engages through the drive device formed by the gearing unit 37 and the drive unit 45, and is supported by way of its lower end in a receptacle in the base of the second housing part 7.

Here, the bar-shaped element 53 jointly performs every rotational movement of the rotor 23, wherein the rotational movement is loaded at most by frictional forces and otherwise takes place in a load-free manner. As a result, there are practically no torsional forces whatsoever within the bar-shaped element, such that the rotational position of the lower end of the bar-shaped element 53 constitutes an exact reproduction of the rotational position of the rotor 23.

It is pointed out at this juncture that said exact reproduction is subject at most to a degree of play that arises as a result of the connection of the rotor 23 to the coupling element 15 via the connecting bolts 25. This is because the receiving bores in the rotor 23 must be slightly larger than the outer diameter of the connecting bolts 25 in order to permit a slight wobbling movement of the rotor 23. This is necessary in order to compensate manufacturing and/or assembly tolerances which result in the face surface of the rotor 23 and the face surface of the stator 29 not being positioned exactly in alignment. Said wobbling movements are made possible by the fact that the rotor 23 rests by way of its lower face surface on the face surface of the compensation element or the wobble bar 21. The latter is dimensioned such that it can be deformed within the required narrow limits by the high axial forces that must be transmitted via the compensation element 21 from the coupling element 15 to the rotor 23.

By contrast, as already stated, the rotational movement of the bar-shaped element 53 takes place in a substantially load-free manner.

In the lower region, that is to say in the rear region of the drive unit 45, there is provided a device 55 for detecting the rotational position of the rotor. Said device comprises a marker element 57 which is connected, in the lower region, to the bar-shaped element 53. For this purpose, the marker element 57 may have a central bore through which the bar-shaped element 53 extends. The fixing may be realized for example by means of adhesive bonding or by means of a knurled screw. Furthermore, the device for detecting the rotational position of the rotor comprises a sensor element 59 which is arranged so as to be situated opposite the circumferential surface of the substantially cylindrical marker element 57. The marker element may for example have magnetic or optical marks or markings along its circumferential surface, the movement or position of which marks or markings is detected by the sensor element 59. The signal of the sensor element 59 may be supplied to an evaluation and control unit (not illustrated in any more detail). The latter can actuate the drive unit 45, as a function of the signal from the device for detecting the rotational position of the rotor 23, such that the rotor 23 is moved in a controlled manner into a predefined rotational position.

The marker element 57 and the sensor element 59 may for example be designed such that magnetic or optical position detection takes place. A suitable sensor element 59 is for example a Hall sensor for detecting magnetic marks of a corresponding magnetic marker element 57. As an optical detector or optical sensor element 59, use may be made, for example, of a photodiode which detects light reflected by the optical marks of the respective optical marker element 57. For this purpose, the optical marks of the marker element 57 may for example also be illuminated by an LED.

In principle, however, any device for detecting the rotational position of the rotor is suitable which is capable of detecting the circumferential position or circumferential movement of the transmission element 51 in the form of the bar-shaped element 53 and generating a corresponding signal.

As a result of the provision of corresponding marks on the marker element 57, it is possible here to determine both the absolute rotational position and also the relative rotational position in relation to a predefined initial value.

In an embodiment which is not illustrated, the device 55 for detecting the rotational position of the rotor may also be designed such that the transmission element 51 or the bar-shaped element 53 actuate a potentiometer, preferably the sliding contact of a potentiometer. Even though, in this embodiment, the position detection does not take place in a contactless manner, it can be realized in an extremely simple and inexpensive form.

Figure 3:
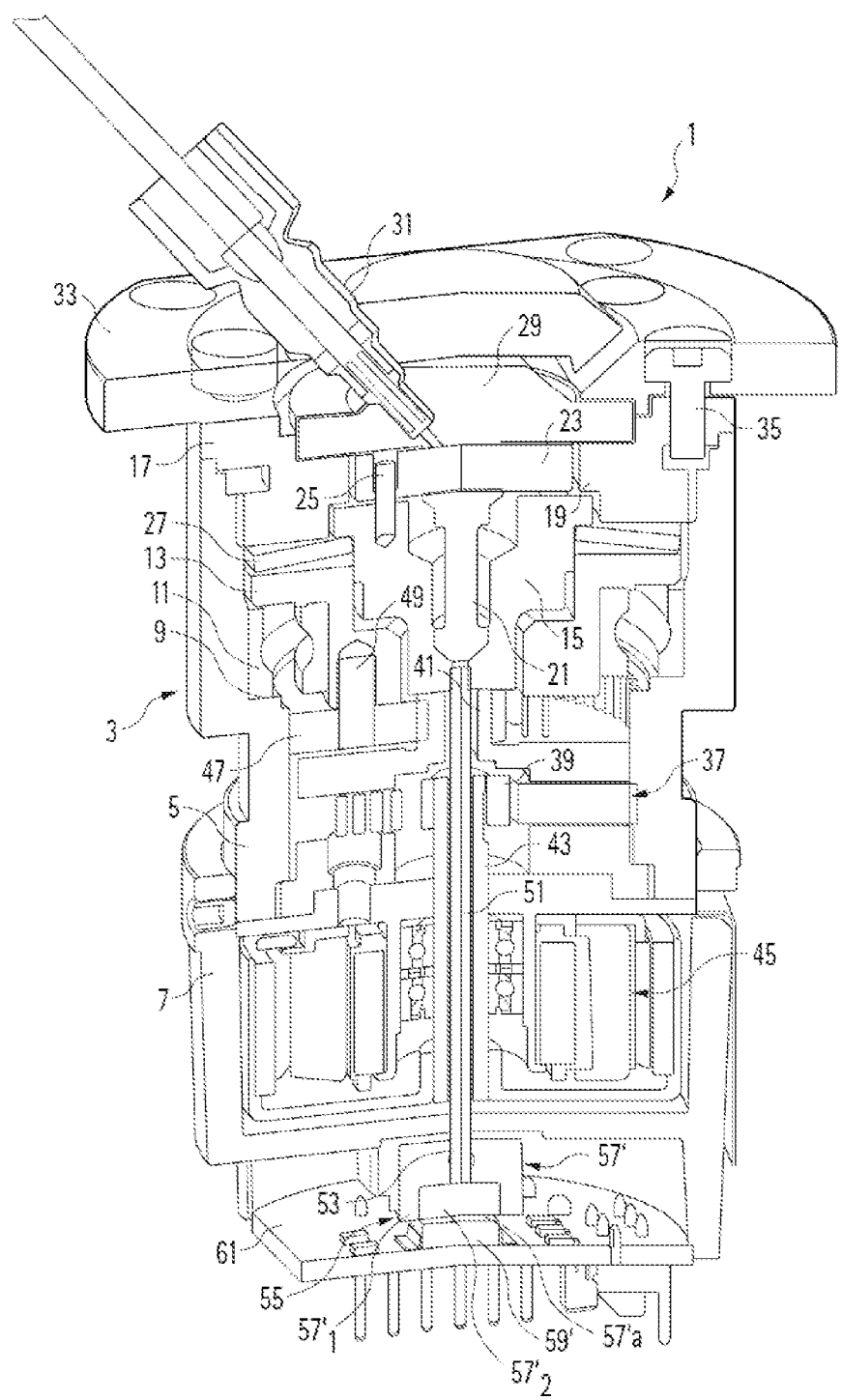
FIG. 3 is a perspective, cut-away illustration of a further embodiment of a switching valve according to the invention.

The embodiment of a switching valve 1 illustrated in FIG. 3 differs from the embodiment as per FIG. 1 substantially merely in that the device for detecting the rotational position of the rotor is arranged not radially at the lower end of the bar-shaped element 53 but rather axially. For this purpose, the device 53 comprises a marker element 57' which, in turn, has a coaxial bore into which the lower end of the bar-shaped element 53 engages. In the case of this marker element 57', however, the marker surface itself or the markings are provided not on the radially outwardly pointing circumferential surface, as is the case in the embodiment as per FIG. 1, but rather on the downwardly directed face surface 57'$a$ thereof.

As illustrated in FIG. 2, the marker element 57' may also be formed in two parts and have a receiving part 57$_1$ which, on the face side, has a pot-shaped recess in which the marker element itself, for example a radially magnetized permanent magnet 57'$_2$, is arranged and held.

The retention and guidance of the bar-shaped element 53 is realized in the exemplary embodiment illustrated in FIG. 3 merely by the fastening to the coupling element 15 and by means of the engagement through the drive output shaft 43 and through the sun gears 39 and 41. The mounting and guidance of the bar-shaped element 52 may however also be realized additionally or exclusively in the housing part 7.

Opposite the face surface 57'$a$ of the marker element 57' there is arranged a sensor element 59' in the form of a Hall sensor chip which is capable of detecting the magnetic marker (radially running) of the radially magnetized permanent magnet 57$_2$. The sensor element 59' is provided on a printed circuit board 61 on which are also provided the electronics for the evaluation and generation of a signal which represents the absolute or relative position of the rotor 23.

Since the device 55 or the evaluation electronics is situated at the axially rear end region of the switching valve 1, it is possible in all of the embodiments as per FIGS. 1 to 3 for the switching valve to be inserted by way of its front head region (for example including the entire first housing part 5) into a wall of a column oven. Owing to the position of the device 55, the sensor device and/or corresponding evaluation electronics are prevented from being exposed to inadmissibly high temperatures.

It is pointed out here that it is self-evidently also possible in the embodiment as per FIG. 1 for evaluation electronics or detection electronics for generating a suitable analogue or digital signal, which represents the position of the rotor in the form of a digital or analogue signal, to be provided in the lower base region of the second housing part 7.

Furthermore, said structural form has the advantage that the device for detecting the rotational position of the rotor is provided axially in the rear region, and a highly compact structural form can be attained overall. In particular, the structural form is not increased with regard to its radial extent by the provision of a corresponding device 55. This makes it possible for multiple such switching valves 1 to be positioned, for example inserted into the wall of a column oven, with a very small spacing between their axes.

What is claimed is:

1. A switching valve for liquid chromatography comprising:
   (a) a stator including a plurality of ports and a stator face surface, each port having a predetermined port opening cross section at the stator face surface;
   (b) a rotor including a rotor face surface, the rotor face surface pressed against the stator face surface, the rotor face surface having at least one or more grooves, in which the switching valve has a predetermined switching position where one of the grooves connects the predetermined port opening cross sections in a pressure-tight manner, the rotor and the stator both being at an axially front region of the switching valve;
   (c) a drive device configured to rotate the rotor; and
   (d) a device for detecting a rotational position of the rotor and generating a signal corresponding to an absolute or a relative rotational position of the rotor, the device being situated in an axially rear region of the switching valve, in which the device for detecting a rotational position of the rotor comprises a transmission element, the transmission element being coupled rotationally conjointly to the rotor, and the transmission element being movable in a substantially load-free manner.

2. The switching valve of claim 1, in which the transmission element is coupled rotationally conjointly to a coupling element, and the coupling element is coupled rotationally conjointly to the rotor.

3. The switching valve of claim 1, in which the transmission element comprises a bar-shaped element.

4. The switching valve of claim 1, the device being configured to detect a rotational position of the transmission element in a region facing away from the rotor.

5. The switching valve of claim 1, in which the axially rear region of the switching valve is thermally decoupled with the axially front region of the switching valve.

6. The switching valve of claim 1, in which the transmission element comprises a thermally insulating material.

7. The switching valve of claim 6, in which the thermally insulating material is a material selected from the group consisting of a plastic and a ceramic.

8. The switching valve of claim 1, in which the drive device is axially adjacent to the rotor and in that the transmission element extends axially through the drive device.

9. The switching valve of claim 2, in which the drive device is axially adjacent to the coupling element and in that the transmission element extends axially through the drive device.

10. The switching valve of claim 3, in which the bar-shaped transmission element extends through a hollow drive output shaft of the drive device.

11. The switching valve of claim 10, in which the drive device includes a planetary gear set which faces toward the rotor in an axial direction, and in that the bar-shaped transmission element extends through one or more sun gears of the planetary gear set.

12. The switching valve of claim 1, in which the device for detecting a rotational position of the rotor is arranged radially in a region of a rear end of the transmission element.

13. The switching valve of claim 1, in which the device for detecting a rotational position of the rotor is arranged on a face side at a rear end of the transmission element.

14. The switching valve of claim 13, in which the device for detecting a rotational position of the rotor includes a marker element arranged rotationally conjointly on a rear end of the transmission element and a sensor element configured to detect an absolute or a relative rotational position of the marker element.

15. The switching valve of claim 14, in which the marker element is a magnet element and the sensor element is a Hall sensor element, a face surface of the Hall sensor element is situated opposite a face surface of the magnet element and detects the rotational position thereof contactlessly.

\* \* \* \* \*